(12) United States Patent
Han et al.

(10) Patent No.: US 11,510,683 B2
(45) Date of Patent: Nov. 29, 2022

(54) FISTULA BANDAGE

(71) Applicant: Zhongshan Hospital Xiamen University, Xiamen (CN)

(72) Inventors: Wei Han, Xiamen (CN); Rongrong Zong, Xiamen (CN); Yilin Deng, Xiamen (CN); Tianjun Guan, Xiamen (CN); Qiuying Han, Xiamen (CN); Lan Chen, Xiamen (CN)

(73) Assignee: ZHONGSHAN HOSPITAL XIAMEN UNIVERSITY, Xiamen (CN)

( * ) Notice: Subject to any disclaimer, the term of this patent is extended or adjusted under 35 U.S.C. 154(b) by 479 days.

(21) Appl. No.: 16/706,682

(22) Filed: Dec. 7, 2019

(65) Prior Publication Data
US 2020/0187959 A1 Jun. 18, 2020

(30) Foreign Application Priority Data

Dec. 13, 2018 (CN) .......................... 201822097367.6

(51) Int. Cl.
*A61B 17/132* (2006.01)
*A61F 13/00* (2006.01)
*A61M 1/36* (2006.01)

(52) U.S. Cl.
CPC .......... *A61B 17/1327* (2013.01); *A61F 13/00* (2013.01); *A61M 1/3655* (2013.01); *A61F 2013/0028* (2013.01)

(58) Field of Classification Search
CPC ........ A61F 13/00; A61F 13/108; A61F 13/10; A61B 17/132–1327; A61B 17/12; A61B 2017/12004; A61B 17/00; A44B 11/065; A44B 11/06–125; Y10T 24/2187; Y10T 24/21; A44C 5/18–246
See application file for complete search history.

(56) References Cited

FOREIGN PATENT DOCUMENTS

| CN | 202096249 U | * | 1/2012 | |
| CN | 103637875 A | * | 3/2014 | ............. A61F 13/00 |

* cited by examiner

*Primary Examiner* — Nicholas J. Weiss
*Assistant Examiner* — Linnae E. Raymond

(57) ABSTRACT

A fistula bandage comprising a bandage and an adjustment device for adjusting a tension of the bandage, where the adjustment device comprises: a first engagement portion connected to a first end of the bandage; and a second engagement portion connected to a second end of the bandage; wherein the second engagement portion comprises: a base having a first sliding slot and connected to the second end of the bandage; a moving member slidingly engaged with the base and connected to the first engagement portion; a driving mechanism supported on the base and driving the moving member to slide in a first direction relative to the base; and a stopping mechanism connected to the driving mechanism. The driving mechanism drives the first engagement portion to move relative to the second engagement portion, thereby achieving the purpose of adjusting the tension of the bandage.

14 Claims, 6 Drawing Sheets

FISTULA BANDAGE

CROSS-REFERENCE TO RELATED APPLICATIONS

The present application claims the benefit under 35 U.S.C. § 119 of China Patent Application No. 201822097367.6, filed on Dec. 13, 2018 in the China National Intellectual Property Administration, the content of which is hereby incorporated by reference.

TECHNICAL FIELD

The present disclosure relates to the field of medical equipment, in particular to a fistula bandage.

BACKGROUND

For long-term hemodialysis treatment (2-3 times/week), patients with vasomotor arteriovenous fistula (hereinafter referred to as fistula) is the most commonly used vascular access. Most patients in China is treated using this method. Fistula is considered the lifeline of patients undergoing hemodialysis treatment. In the hemodialysis patients, the arteriovenous fistula is located in the forearm or upper arm of the upper limb of the patient and is composed of a vascular graft or an autologous blood vessel. At the end of each hemodialysis treatment, it is important for the patient selects an appropriate method for compression hemostasis of the puncture injury. At present, artificial compression or bandage compression is used as hemostasis method globally. The existing bandage only relies on hook and loop fastener (Velcro™) for sticking. When the bandage is too tight or too loose, direct fine tune is impossible. It is necessary to tear the hook and loop fastener (Velcro™) apart for re-adjustment, and the tightness of the adjustment is not well controlled.

SUMMARY

One object of the present disclosure is to provide a fistula bandage with adjustable tightness.

A fistula bandage comprising a bandage and an adjustment device for adjusting a tension of the bandage, characterized in that the adjustment device comprises: a first engagement portion connected to a first end of the bandage; and a second engagement portion connected to a second end of the bandage; wherein the second engagement portion comprises: a base having a first sliding slot extending in a first direction and connected to the second end of the bandage; a moving member slidingly engaged with the base and connected to the first engagement portion; a driving mechanism supported on the base and driving the moving member to slide in a first direction relative to the base to adjust the tension of the bandage; and a stopping mechanism connected to the driving mechanism and fixing the moving member when the driving mechanism does not drive the moving member to slide.

Preferably, the driving mechanism comprises a rack member fixed to the moving member and extending in the first direction, and a gear member rotatably supported on the base by a rotating shaft; the gear member is caused to engage with or move away from the rack member under an external force, and the stopping mechanism is caused to engage with a tooth groove on the rack member or move away from the rack member under an external force.

Preferably, the base is a housing having a first accommodating chamber in which the moving member, the driving mechanism and the stopping mechanism are accommodated; and the gear member passes through a first opening formed on the base and is partially exposed outside the base, and the moving member passes through a second opening formed on the base for connecting to the first engagement portion.

Preferably, a direction directed to an end surface of the rack member that is distributed with teeth is defined as a second direction, he gear member is movable along the second direction and is caused to engage with or move away from the rack member under an external force; and the driving mechanism comprises a buffer assembly; wherein the buffer assembly comprises: a support member sleeved on a limiting slot opened on the base and extending in the second direction; and an elastic member sandwiched between the support member and a slot bottom of the limiting slot; the gear member is rotatably supported on the support member via a rotating shaft.

Preferably, the driving mechanism comprises two sets of buffer assemblies disposed on opposite sides of the gear member along an axial direction of the gear member.

Preferably, the stopping mechanism comprises a stopping member; and a lever assembly comprising a link having one end connected to the stopping member and the other end hinged to the driving mechanism and a lever seat having one end secured to the base and the other end hinged to the link.

The present disclosure can achieve the following technical effects:

1. The fistula bandage provided by the present application has an adjustment device for adjusting the tension of the bandage, and the adjustment device has a first engagement portion connected to the first end of the bandage and a second engagement portion. The driving mechanism having the gear and the rack member disposed on the second engagement portion drives the first engagement portion to move relative to the second engagement portion, thereby achieving the purpose of adjusting the tension of the bandage.

2. The second engagement portion of the fistula bandage provided by the present application is provided with a stopping mechanism designed according to leverage principle, and the stopping mechanism is used together with the buffer assembly on the driving mechanism, so that when the gear member drives the rack member to move, the stopping member on the stopping mechanism does not contact with the rack member. When the gear member is disengaged from the rack member by the driving of the buffer member, the stopping member is engaged with a tooth groove of the rack member to fix the first engagement portion.

DETAILED DESCRIPTION OF EMBODIMENTS

Figure 1:
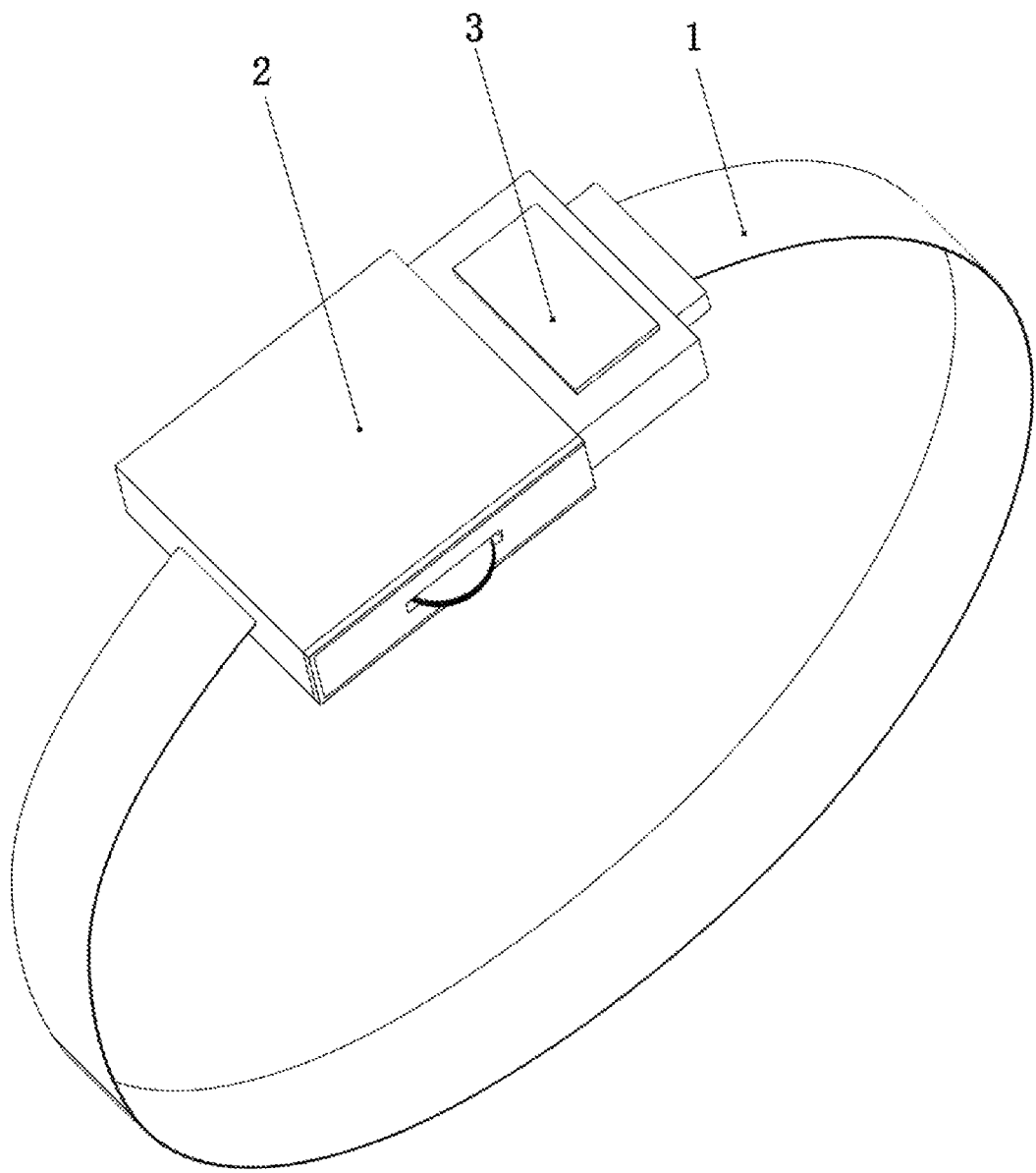
FIGS. 1 and 2 are schematic views of the fistula bandage of the present disclosure.

The embodiments of the present disclosure will be clearly and completely described in conjunction with the drawings of the embodiments of the present disclosure. Apparently, what is described are some but not all of the embodiments of the present disclosure. All other embodiments obtained by a person of ordinary skill in the art based on the embodiments of the present disclosure without creative efforts are within the scope of the present disclosure. Therefore, the following detailed description of the embodiments of the present disclosure are not intended to limit the scope of the present disclosure, but to explain the selected embodiments of the present disclosure. All other embodiments obtained by a person of ordinary skill in the art based on the embodiments of the present disclosure without creative efforts are within the scope of the present disclosure.

In the description of the present disclosure, it is to be understood that the orientational or positional relationships indicated by the terms "center", "longitudinal", "transversal", "length", "width", "thickness", "upper", "lower", "front", "rear", "left", "right", "vertical", "horizontal", "top", "bottom", "inside", "outside", "clockwise", "counterclockwise", etc. are based on the orientation or positional relationship shown in the drawings, are merely for the convenience of describing the present disclosure and simplifying the description, and do not indicate or imply that the device or component referred to must have a specific orientation or be constructed and operated in a specific orientation. Therefore, it should not be construed as limiting the present disclosure.

The structure and function of the solution of the present application will now be described in detail with reference to FIGS. 1 to 6.

With reference to FIGS. 1 to 6, a first embodiment of the present disclosure provides a fistula bandage, which comprises a bandage 1 and an adjustment device for adjusting a tension of the bandage 1. Referring to FIGS. 1 to 4, the adjustment device comprises a first engagement portion 3 and a second engagement portion 2. The first engagement portion 3 is connected to the first end portion of the bandage 1 and the second engagement portion 2 is connected to the second end portion of the bandage 1. The first engagement portion 3 comprises a first fastening assembly 9 connected to the first end of the bandage 1 and a second fastening assembly 8 for fastening or disengaging the first fastening assembly. The second fastening assembly 8 is connected to the moving member 5. In other embodiments, the second fastening assembly 8 and the moving member 5 may be integrally formed.

Figure 4:
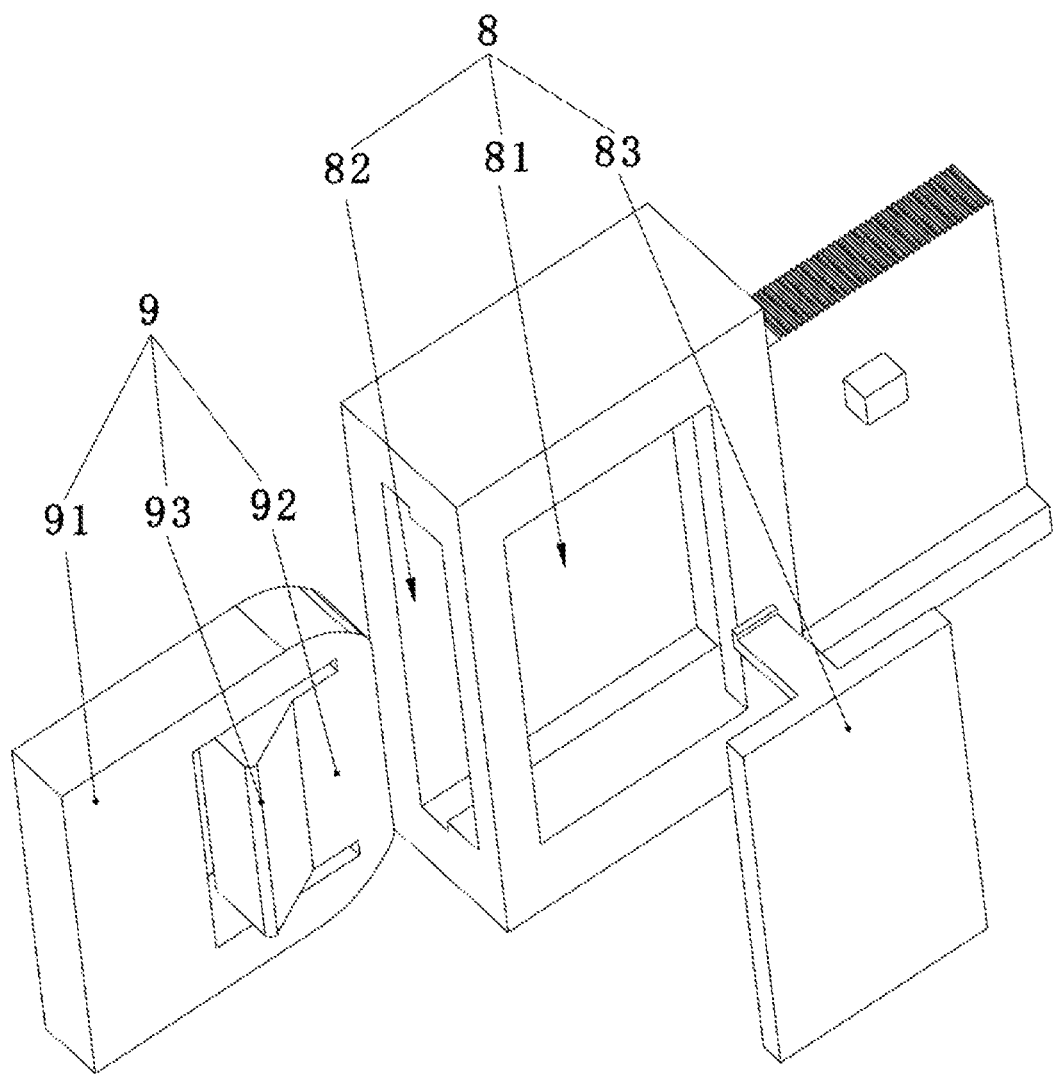
FIG. 4 is a schematic view of the first engagement portion of the present disclosure.
Figure 5:
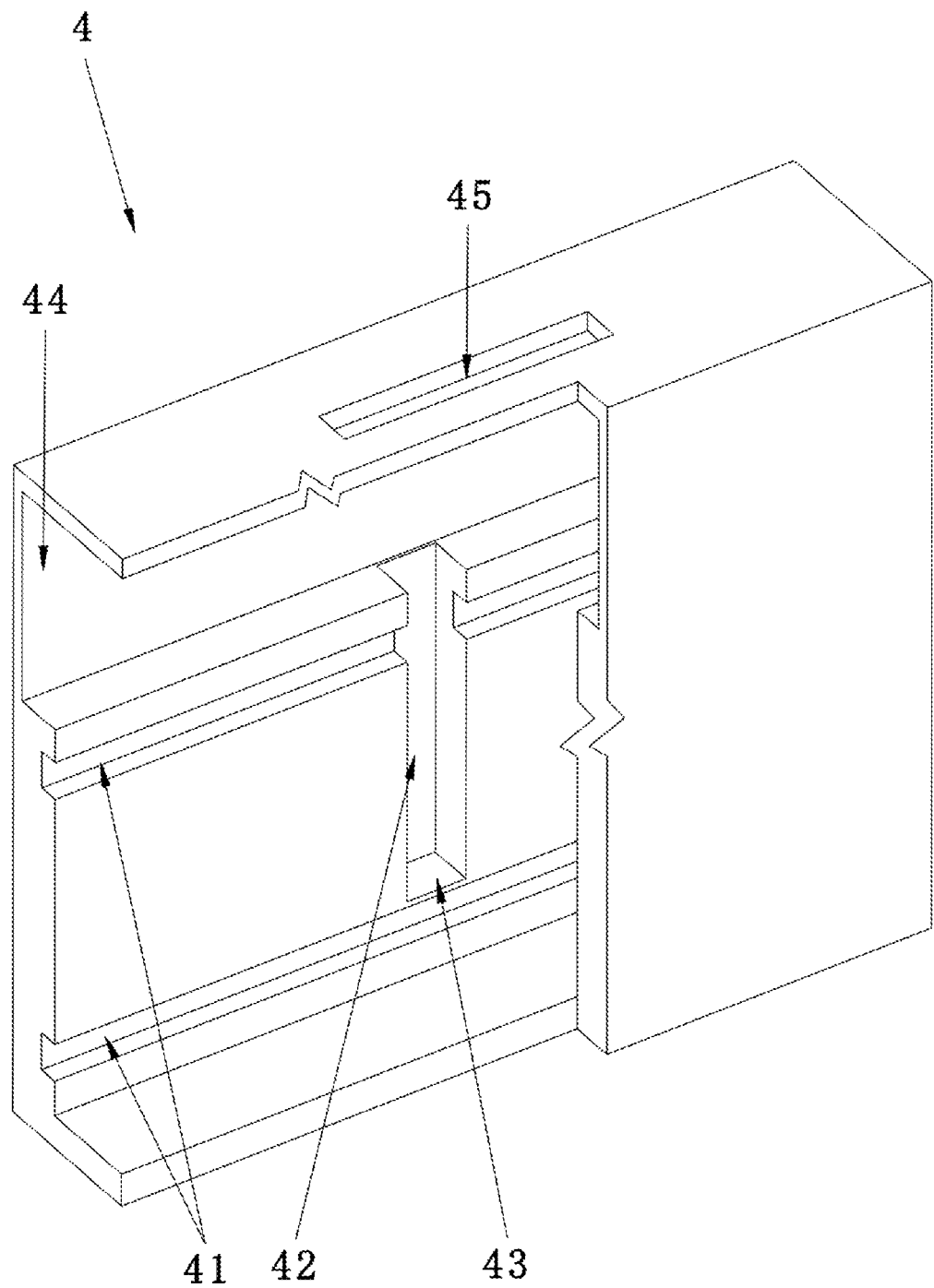
FIG. 5 is a schematic view of the base of the present disclosure.

Referring to FIG. 4, the second fastening assembly 8 comprises a second housing having a third opening 82 and a second accommodating chamber. The front side of the second housing is provided with a fourth opening 81 where a button 83 is configured. The third opening is directed to the first direction. The first fastening assembly 9 comprises a bracket 91 and an elastic wall 92 supported on the bracket 91 at one end. The other end of the elastic wall 92 moves backwards under force, and the thickness of the elastic wall 92 in the front-rear direction is smaller than the thickness of the bracket 91. The upper side of the elastic wall 92 has an upwardly convex bulge 93 which abuts against the end edge of the fourth opening 81 when the first fastening assembly 9 is inserted into the second accommodating chamber through the third opening 82, for secured connection with the second fastening assembly 8. The button 83 located at the fourth opening 81 presses against the elastic wall 92 under force to cause the elastic wall to move rearward to separate the first fastening assembly 9 and the second fastening assembly 8. It is understood that the first direction and the second direction in the present embodiment are based on the orientation or positional relationship shown in the drawings, are merely for convenience of describing the present disclosure and simplifying the description, and do not indicate or imply that the indicated device or component must have a particular orientation or are constructed and operated in a particular orientation, and thus are not to be construed as limiting the present disclosure.

Figure 2:
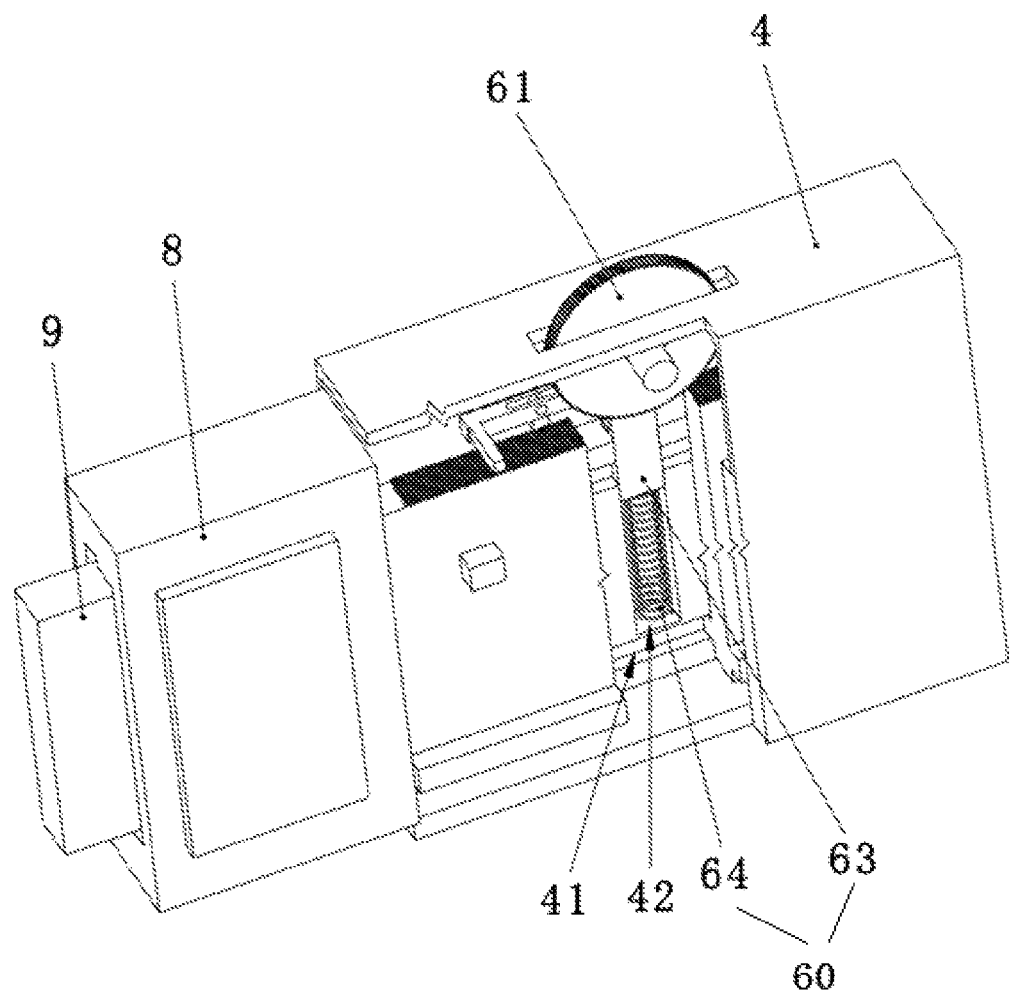
Figure 3:
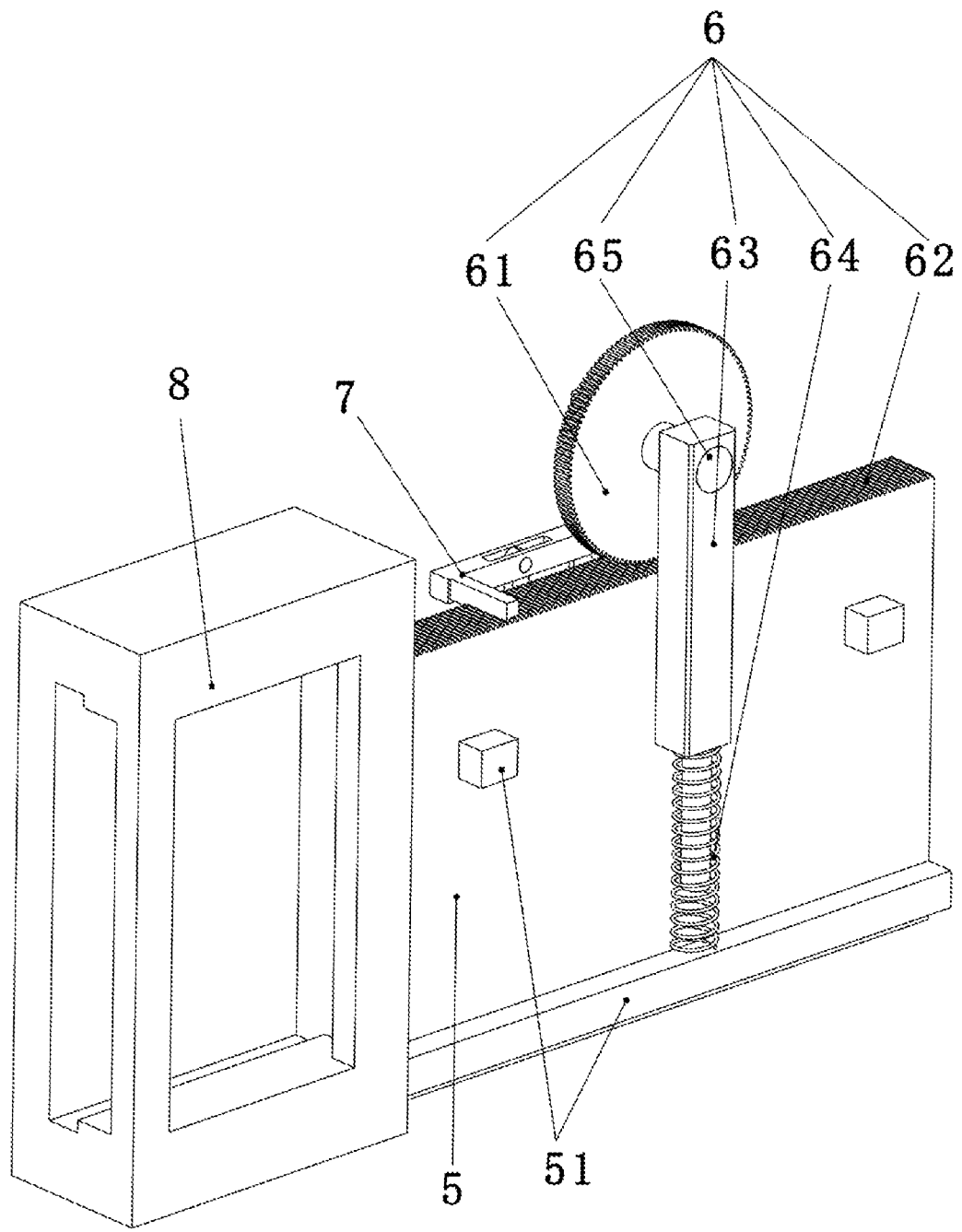
FIG. 3 is a schematic view of the second engagement portion of the present disclosure.

Referring to FIGS. 2 to 4, the second engagement portion 2 comprises a base 4, a moving member 5, a driving mechanism 6, and a stopping mechanism 7. The base 4 has a first sliding slot 41 extending in a first direction, and the base 4 is connected to the second end of the bandage 1. The moving member 5 is slidably engaged with the base 4 and connected to the first engagement portion 3. The moving member 5 is provided with a slider 51 adapted to the first sliding slot 41. The driving mechanism 6 is supported on the base 4 and drives the moving member 5 to slide in the first direction with respect to the base 4 to adjust the tension of the bandage 1. The stopping mechanism 7 is connected to the driving mechanism 6 and fixes the moving member 5 when the driving mechanism 6 does not drive the moving member 5 to slide.

Referring to FIGS. 2 and 3, in the present embodiment, the driving mechanism 6 comprises a rack member 62 fixed to the moving member 5 and extending in the first direction and a gear member 61 rotatably supported on the base 4 by a rotating shaft 65. The gear member 61 engages with or is away from the rack member 62 under an external force. The stopping mechanism 7 is caused to engage with a tooth groove on the rack member 62 or move away from the rack member under an external force.

In this embodiment, referring to FIGS. 2 to 4, the base 4 is a housing having a first accommodating chamber in which and the moving member 5, the driving mechanism 6 and the stopping mechanism 7 are accommodated. The gear member 61 passes through the first opening 45 opened on the base 4 and is partially exposed outside the housing, and the moving member 5 passes through the second opening 44 opened in the housing for connecting the first engagement portion 3. Rotating the part of the gear member 61 exposed to the outside of the base 4, the rack member 62 that meshes with the gear member 61 can be driven to move in the first direction, thereby controlling the tightness of the bandage 1 having two ends connected respectively to the first engagement portion 3 and the second engagement portion 2.

In the present embodiment, a direction directed to an end surface of the rack member that is distributed with teeth is defined as a second direction, and the gear member is movable along the second direction and is caused to engage with or move away from the rack member under an external force. Referring to FIGS. 2 and 3, the driving mechanism 6 comprises a buffer assembly 60. The buffer assembly 60 comprises a support member 63 and an elastic member 64. A limiting slot 42 extending in the second direction is defined in the base 4, and the supporting member 63 is sleeved in the limiting slot 42. The elastic member 64 is sandwiched between the support member 63 and the slot bottom 43 of the limiting slot 42. One end of the support member 63 abuts against the elastic member 64 and the other end abuts against the inner portion of the first accommodating chamber. The inner wall of the first accommodating chamber abutting one end of the support member 63 further limits the travel distance of the support member 63. It can be understood that the gear member 61 of the present disclosure does not mesh with the rack member 62 when a force is not applied, and the gear member 61 moves in the second direction and compresses the elastic member 64 through the support member 63 when a force is applied. The movable gear member 61 is meshed with the rack member 62 under an external force, and the gear member 61 is rotated to drive the rack member 62 to move in the first direction. The gear member 61 is rotatably supported on the support member 63 via a rotating shaft 65, and the rotating shaft 65 is rotatable relative to the supporting member 63.

In the present embodiment, the driving mechanism 6 comprises two sets of buffering assemblies 60 which are disposed on opposite sides of the gear member 61 along the axial direction of the gear member 61 and supported on the base 4. Two sets of buffer assemblies 60 provide a more stable support. It will be appreciated that in other embodiments, there may be only one set of buffer assemblies 60.

Figure 6:
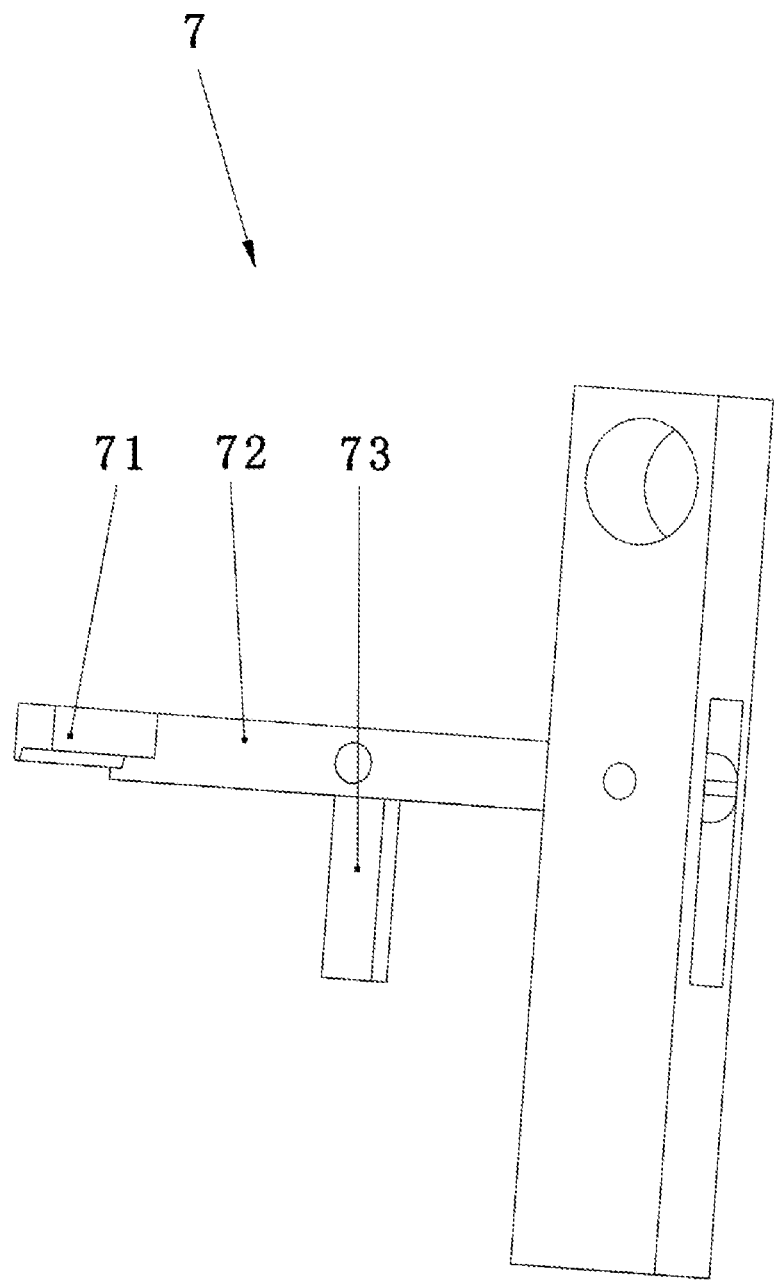
FIG. 6 is a schematic view of the stopping mechanism of the present disclosure.

In the present embodiment, referring to FIGS. 2 to 3 and FIG. 6, the stopping mechanism 7 comprises a stopping member 71 and a lever assembly. The lever assembly comprises a link 72 having one end connected to the stopping member 71 and the other end hinged to the driving mechanism 6 and a lever seat 73 having one end secured to the base 4 and the other end hinged to the link 72. The stopping member 71 comprises a snap member extending in a direction that coincides with the direction in which the tooth slot of the rack member 62 extends. The snap member is inserted into a tooth slot of the rack member 62 to fix the moving member 5 so that it cannot move.

Referring to FIGS. 1 to 6, when the second engagement portion 2 of the present embodiment is in use, the gear member 61 disposed thereon is forced to move downward in the second direction, and the downwardly moving gear member 61 pushes the support member 63 to move downward. The support member 63 drives one end of the link 72 hinged thereto to move downward together, and the other end of the link 72 to which the stopping member 71 is connected moves upward under the support of the lever seat 73, so that the stopping member 71 is disengaged from the tooth slot of the rack member 62 while the gear member 61 is meshed with the rack member 62 so that the rack member 62 can be driven to move. When the external force exerted on the gear member 61 is removed, the support member 63 moves upward in the second direction under the force of the elastic member 64, so that the gear member 61 is disengaged from the engagement with the rack member 62, one end of the link 72 connected to the support member 63 moves upward, and the other end of the link 72 to which the stopping member 71 is connected moves downward under the support of the lever seat 73 and is engaged in the engaging slot of the rack member 62.

The above is only preferred embodiments of the present disclosure and is not intended to limit the present disclosure. Various modifications and changes can be made by those skilled in the art. Any modifications, equivalent substitutions, improvements, etc. made within the spirit and scope of the present disclosure are intended to be comprised within the scope of the present disclosure.

What is claimed is:

1. A fistula bandage comprising a bandage and an adjustment device for adjusting a tension of the bandage, the adjustment device comprises:
    a first engagement portion connected to a first end of the bandage; and
    a second engagement portion connected to a second end of the bandage;
    wherein the second engagement portion comprises:
        a base having a first sliding slot extending in a first direction and connected to the second end of the bandage;
        a moving member slidingly engaged with the base and connected to the first engagement portion;
        a driving mechanism supported on the base and driving the moving member to slide in the first direction relative to the base to adjust the tension of the bandage; and
        a stopping mechanism connected to the driving mechanism and fixing the moving member when the driving mechanism does not drive the moving member to slide;
        wherein the driving mechanism comprises a rack member fixed to the moving member and extending in the first direction, and a gear member rotatably supported on the base by a rotating shaft;
        the gear member is configured to engage with or move away from the rack member under an external force; and
        the stopping mechanism is configured to engage with or move away from a tooth groove on the rack member under an external force.

2. The fistula bandage according to claim 1, wherein the base is a housing having a first accommodating chamber in which the moving member, the driving mechanism and the stopping mechanism are accommodated; and the gear member passes through a first opening formed on the base and is partially exposed outside the base, and the moving member passes through a second opening formed on the base for connecting to the first engagement portion.

3. The fistula bandage according to claim 2, wherein a direction directed to an end surface of the rack member that is distributed with teeth is defined as a second direction, the gear member is movable along the second direction and is caused to engage with or move away from the rack member under an external force; and the driving mechanism comprises a buffer assembly; wherein the buffer assembly comprises: a support member sleeved on a limiting slot opened on the base and extending in the second direction; and an elastic member sandwiched between the support member and a slot bottom of the limiting slot; the gear member is rotatably supported on the support member via a rotating shaft.

4. The fistula bandage according to claim 3, wherein a first sliding slot extending in the first direction is opened on the base, and the moving member is provided with a slider adapted to the first sliding slot so that the moving member is slidable relative to the base in the first direction.

5. The fistula bandage according to claim 4, wherein two first sliding slots that are parallel to each other and extend in the second direction are opened on the base.

6. The fistula bandage according to claim 5, wherein the limiting slot passes through the first sliding slot that is close to the first opening in the second direction, and the slider, that is away from the tooth groove in the second direction, of the moving member is configured as an elongated structure extending in the first direction.

7. The fistula bandage according to claim 3, wherein in the second direction, two ends of the support member can respectively abut against an inner wall of the first accommodating chamber and the elastic member, to limit a travel distance of the support member.

8. The fistula bandage according to claim 3, wherein the driving mechanism comprises two sets of buffer assemblies disposed on opposite sides of the gear member along an axial direction of the gear member.

9. The fistula bandage according to claim 3, wherein the stopping mechanism comprises a stopping member and a lever assembly comprising a link having one end connected to the stopping member and the other end hinged to the driving mechanism and a lever seat having one end secured to the base and the other end hinged to the link.

10. The fistula bandage according to claim 9, wherein the stopping member is provided with a snap member, and the buffer assembly supports the gear member when the gear member is not subjected to an external force so that the snap member is engaged with a tooth groove of the rack member.

11. The fistula bandage according to claim 3, wherein the first engagement portion comprises a first fastening assembly, the second engagement portion comprises a second fastening assembly, the first fastening assembly is connected to the first end of the bandage and the second fastening assembly is connected to the moving member and the second end of the bandage.

12. The fistula bandage of claim 11, wherein the second fastening assembly is integrally formed with the moving member.

13. The fistula bandage according to claim 11, wherein the second fastening assembly comprises a second housing having a third opening and a second accommodating chamber, a front side of the second housing has a fourth opening, and the second opening is provided with a button; wherein the third opening is directed to the first direction.

14. The fistula bandage according to claim 13, wherein the first fastening assembly comprises a bracket and an elastic wall having an upwardly convex bulge, and the first fastening assembly is secured to the second fastening assembly when the bulge abuts against an end edge of the fourth opening; the button, under force, is able to push the elastic wall to separate the first fastening assembly from the second fastening assembly.

* * * * *